(12) United States Patent
Hanson et al.

(10) Patent No.: US 11,688,509 B2
(45) Date of Patent: Jun. 27, 2023

(54) HEALTH MANAGEMENT SYSTEM

(71) Applicant: SRI International, Menlo Park, CA (US)

(72) Inventors: Mark Hanson, Orinda, CA (US); Bhaskar Ramamurthy, Los Altos, CA (US); Manish Kothari, San Carlos, CA (US); Brecken Hu Uhl, Placitas, NM (US)

(73) Assignee: SRI INTERNATIONAL, Menlo Park, CA (US)

( * ) Notice: Subject to any disclaimer, the term of this patent is extended or adjusted under 35 U.S.C. 154(b) by 478 days.

(21) Appl. No.: 16/744,962

(22) Filed: Jan. 16, 2020

(65) Prior Publication Data

US 2020/0227161 A1 Jul. 16, 2020

Related U.S. Application Data

(60) Provisional application No. 62/793,029, filed on Jan. 16, 2019.

(51) Int. Cl.
*G16H 40/20* (2018.01)
*G16H 70/20* (2018.01)
(Continued)

(52) U.S. Cl.
CPC ......... *G16H 40/20* (2018.01); *G06F 16/2477* (2019.01); *G06N 20/00* (2019.01);
(Continued)

(58) Field of Classification Search
CPC ........ G16H 40/20; G16H 10/60; G16H 50/20; G16H 50/30; G16H 70/20; G16H 10/20; G16H 80/00; G06F 16/2477; G06N 20/00; G06N 3/0472; G06N 5/003; G06N 5/02; G06N 3/006; G06N 3/0445; G06N 3/08;
(Continued)

(56) References Cited

U.S. PATENT DOCUMENTS 8,271,295 B1    9/2012   Miller et al.
8,924,238 B1 * 12/2014   Nidy .................. G16H 40/20
                                                          705/2

(Continued)

FOREIGN PATENT DOCUMENTS

WO      2016/094903 A1    6/2016

*Primary Examiner* — Brian L Albertalli
(74) *Attorney, Agent, or Firm* — Shumaker & Sieffert, P.A.

(57) ABSTRACT

In general, this disclosure describes techniques for a health management system that schedules medical appointments based on a dialog with a user (e.g., a patient), clinical guideline information, and/or other information. The health management system may engage in a dialog with the user, the dialog including requests from the health management system for audio input to the user device and audio input from the user in response to each request. The health management system may extract information from the audio input and compare the extracted information to clinical guideline information to determine one or more probable health conditions of the user. The health management system may determine a time allotment, identify a health care provider type and a platform for a medical appointment based on the one or more probable health conditions.

20 Claims, 8 Drawing Sheets

(51) Int. Cl.
*G16H 50/30* (2018.01)
*G06Q 10/1093* (2023.01)
*G16H 50/20* (2018.01)
*G06F 16/2458* (2019.01)
*G06N 20/00* (2019.01)
*G10L 15/02* (2006.01)
*G10L 15/22* (2006.01)
*G10L 15/00* (2013.01)
*G10L 25/63* (2013.01)
*G10L 15/18* (2013.01)
*G10L 25/66* (2013.01)
*G16H 10/60* (2018.01)
*G10L 15/08* (2006.01)

(52) U.S. Cl.
CPC ........ *G06Q 10/1093* (2013.01); *G10L 15/005* (2013.01); *G10L 15/02* (2013.01); *G10L 15/1815* (2013.01); *G10L 15/22* (2013.01); *G10L 25/63* (2013.01); *G10L 25/66* (2013.01); *G16H 10/60* (2018.01); *G16H 50/20* (2018.01); *G16H 50/30* (2018.01); *G16H 70/20* (2018.01); *G10L 2015/088* (2013.01); *G10L 2015/223* (2013.01)

(58) Field of Classification Search
CPC .... G06N 7/005; G06N 20/10; G06Q 10/1093; G10L 15/005; G10L 15/02; G10L 15/1815; G10L 15/22; G10L 25/63; G10L 25/66; G10L 2015/088; G10L 2015/223; G10L 15/1822

See application file for complete search history.

(56) References Cited

U.S. PATENT DOCUMENTS

| | | | |
|---|---|---|---|
| 10,706,873 B2 | 7/2020 | Tsiartas et al. | |
| 2003/0130870 A1 | 7/2003 | Tsuchimura | |
| 2007/0203761 A1* | 8/2007 | Keen | G16H 20/40 705/5 |
| 2014/0019149 A1* | 1/2014 | Yu | G16H 40/20 705/2 |
| 2014/0074454 A1* | 3/2014 | Brown | G10L 15/08 704/235 |
| 2015/0081327 A1 | 3/2015 | Mooker | |
| 2015/0161535 A1* | 6/2015 | Ptashek | G16H 40/20 705/2 |
| 2015/0302156 A1* | 10/2015 | Parsadoust | G16H 50/20 705/3 |
| 2017/0116378 A1* | 4/2017 | Shaw | G01C 21/3617 |
| 2017/0147764 A1* | 5/2017 | P R | G16H 40/20 |
| 2018/0366143 A1* | 12/2018 | Ashoori | G16H 40/63 |
| 2019/0006033 A1* | 1/2019 | Wolthuis | G16H 50/70 |
| 2019/0027248 A1* | 1/2019 | Kataria | G10L 25/63 |
| 2019/0198169 A1* | 6/2019 | T | G16H 50/50 |
| 2019/0267133 A1* | 8/2019 | Schwarz | G06Q 10/1095 |
| 2019/0347621 A1* | 11/2019 | White | G06N 3/08 |
| 2020/0090132 A1* | 3/2020 | Bender | G06F 16/337 |

* cited by examiner

HEALTH MANAGEMENT SYSTEM

This application claims the benefit of U.S. Provisional Patent Application No. 62/793,029, filed Jan. 16, 2019, the entire contents of which are incorporated herein by reference.

TECHNICAL FIELD

This disclosure relates to computing systems and, more specifically, to a health management system.

BACKGROUND

Health management systems are dependent on acquiring accurate and complete information from patients. For example, most current health management systems receive patient information through a manual process in which a doctor or nurse interacts with the patient and manually enters the information into the health management system. This often results in inaccurate and incomplete information that leads to efficiencies or missed or incorrect diagnoses.

Another source of inefficiency within current health management systems arises in the mismatch of time allotted for a medical appointment and the actual time needed for the medical consultation. Time allotments are often proposed generically and are often overridden by doctors. For example, medical staff (e.g., a nurse or operator) may manually schedule a general medical appointment via a health management system or calendaring software with a fixed time allotment irrespective of the reason for the medical consultation, which may be too short or too long for the purpose of the medical consultation, and doctors sometimes end appointments before the scheduled end time or extend appointments beyond the scheduled end time. Ending appointments before scheduled end times results in under-utilized medical staff and longer wait times for patients to obtain medical appointments. In some cases, the wait times to obtain a medical appointment may extend from a day to several months. Conversely, ending appointments beyond their scheduled end times results in longer wait times at the doctor's office for patients with subsequent appointments on the same day. Medical staff may then be pressured to rush through the subsequent appointments, which may result in misdiagnoses.

SUMMARY

In general, this disclosure describes techniques for a health management system that schedules medical appointments based on a dialog with a user (e.g., a patient), clinical guideline information, and/or other information. For example, the health management system may receive a request for a medical appointment from a user (e.g., a patient) through a user device (e.g., telephone, computer, tablet, or any other communication device). The health management system may engage in a dialog with the user, the dialog including requests from the health management system for audio input to the user device and audio input from the user in response to each request. The health management system may extract information from the audio input (including patient symptom information) and compare the extracted information to clinical guideline information to determine one or more probable health conditions of the user. Additionally or alternatively, the health management system may compare the guideline information to at least one of electronic health data associated with the user (e.g., electronic health records (EHRs) or other data about the user that is relevant for diagnosing and/or treating the user), epidemiological data, or local area data to determine one or more probable health conditions of the user. The health management system may determine a time allotment (e.g., date, time, and a duration), identify a health care provider type (e.g., a primary care physician, a specialist, or a nurse practitioner) and a platform (e.g., in-person consultation, video consultation, telephone consultation, chat consultation, email consultation) for a medical appointment based on the one or more probable health conditions. In some examples, the health management system may identify a health care provider based on that provider's schedule and/or skills or experience with the user's probable health condition. In some examples, the health management system may also determine one or more features about the user based on the extracted information and modify the time allotment for the medical appointment based on the one or more features. The health management system may be implemented using a computing system.

As described herein, the health management system may process clinical guidelines to generate the guideline information. For example, the health management system may receive clinical guidelines in the form natural language text and/or flow charts as input, extract a plurality of guideline key phrases from the clinical guidelines, and normalize the plurality of guideline key phrases into normalized guideline expressions. These normalized guideline expressions may include the guideline information that is compared or applied to the extracted information of the audio input from the user. In some examples, the health management system may identify the most relevant clinical guidelines (e.g., the most relevant guideline expressions) as the guideline information to compare to the extracted information of the audio input. In some examples, the health management system may rank the most relevant clinical guidelines to compare to the extracted information of the audio input. In some examples, the health management system may identify the most relevant clinical guideline based on health data, epidemiological data, and/or local area data. In this way, the health management system uses the most relevant clinical guideline to determine probable health conditions or one or more clinical inferences. In some examples, feedback information may be entered into the health management system after the medical appointment to improve time allotments and the identification of relevant clinical guidelines. In some examples, the health management system stores the audio input within the electronic health data associated with the user.

The techniques of this disclosure involve one or more technical improvements to health management systems that provide at least one practical application. For example, a health management system as described herein may schedule medical appointments with more accurate time allotments to better utilize medical personnel, properly diagnose patients, and reduce wait times. Moreover, a health management system as described herein may process natural language or flow chart clinical guidelines to form normalized guidelines expressions that may be compared to extracted information from audio input from a user. In this way, the health management system may determine one or more potential medical conditions to identify an appropriate type of health care provider and platform, and to determine more accurate time allotments for medical appointments.

In some examples, a method for automatically scheduling medical appointments including outputting, by a computing system, one or more requests for audio input to a user;

receiving, by the computing system, the audio input in response to each of the one or more requests; extracting, by the computing system, patient symptom information from the audio input; applying, by the computing system, guideline information to the extracted patient symptom information to determine one or more probable health conditions for the user; determining, by the computing system, a time allotment for a medical appointment for the user based at least on the one or more probable health conditions for the user; identifying, by the computing system, a health care provider type for the medical appointment for the user based at least on the one or more probable health conditions and the time allotment; and providing, by the computing system, a suggested time slot for the medical appointment with a health care provider having the health care provider type for the time allotment.

In some examples, a computing system for automatically scheduling medical appointments, the computing system including processing circuitry coupled to a memory; a dialog manager executing on the processing circuitry and configured to output one or more requests for audio input to a user and receive the audio input in response to each of the one or more requests; a speech analysis module executing on the processing circuitry and configured to extract patient symptom information from the audio input; a machine learning engine executing on the processing circuitry and configured to apply guideline information to the extracted patient symptom information to determine one or more probable health conditions for the user; and a resource management module executing on the processing circuitry and configured to: determine a time allotment for a medical appointment for the user based at least on the one or more probable health conditions for the user; identify a health care provider type for the medical appointment for the user based at least on the one or more probable health conditions and the time allotment; and provide a suggested time slot for the medical appointment with a health care provider having the health care provider type for the time allotment.

In some examples, a non-transitory computer-readable medium comprising instructions for causing processing circuitry of a computing system to perform operations including output one or more requests for audio input to a user; receive the audio input in response to each of the one or more requests; extract patient symptom information from the audio input; apply guideline information to the extracted patient symptom information to determine one or more probable health conditions for the user; determine a time allotment for a medical appointment for the user based at least on the one or more probable health conditions for the user; identify a health care provider type for the medical appointment for the user based at least on the one or more probable health conditions and the time allotment; and provide a suggested time slot for the medical appointment with a health care provider having the health care provider type for the time allotment.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1:
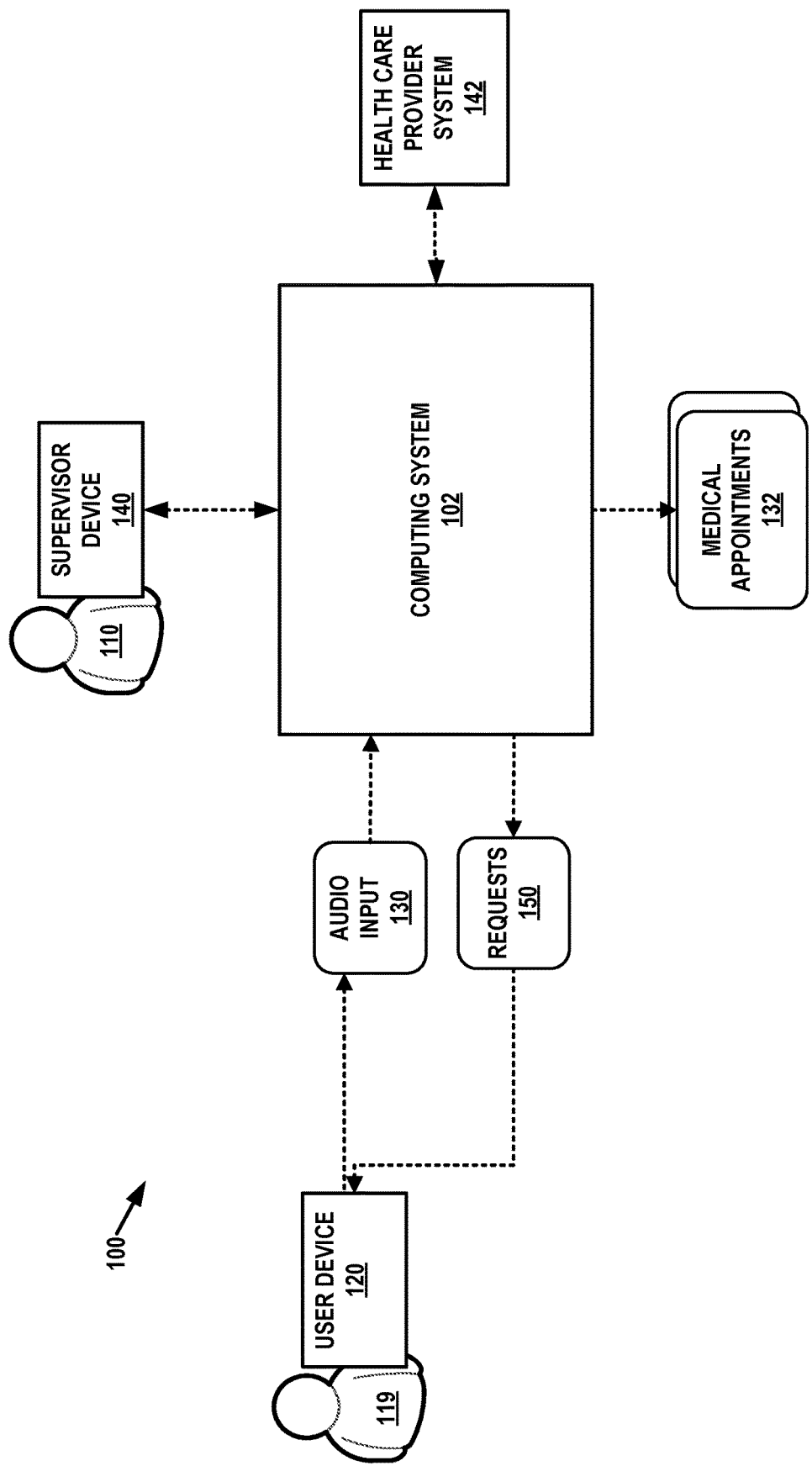
FIG. 1 is a block diagram illustrating an example health management system for scheduling medical appointments, in accordance with techniques of this disclosure.

FIG. 1 is a block diagram illustrating an example an example health management system 100 for scheduling medical appointments 132, in accordance with techniques of this disclosure. System 100 includes at least one user device 120 with which user 119 may use to interact with computing system 102 and, in some cases, with supervisor device 140 or health care provider system 142.

In some examples, computing system 102 represents a server, workstation, desktop or laptop computer, cloud computing system, server farm, and/or server cluster (or portion thereof) that provides services to client devices and other devices or systems. In other examples, computing system 102 may represent or be implemented through one or more virtualized computer instances (e.g., virtual machines, containers) of a data center, cloud computing system, server farm, and/or server cluster. In some examples, computing system 102 may be referred to as a Central Computation Resource (CCR).

User device 120 may represent a telephone, a conferencing device, a desktop or laptop computer, a smartphone, a tablet computer, a voice recorder, smart watch, Intelligent Assistant application or appliance (e.g., Alexa or Google Home) or other device for generating audio signals from utterances by user 119. User device 120 may execute a conferencing application, a Voice over Internet Protocol (VoIP) application, a Video over IP application, a video conferencing application, an Internet-based video conference application, or a telephone application. User device 120 may include one or more input devices to receive utterances from the users and convert the utterances to audio signals. The audio signals generated by user device 120 are represented by audio input 130. While a single representation of a user device 120 and user 119 pair is shown in FIG. 1, additional users with other user devices may concurrently interact with computing system 102 to schedule medical appointments 32.

Supervisor device 140 may represent a telephone, a conferencing device, a desktop or laptop computer, a smartphone, a tablet computer, or any other device for monitoring interactions between user device 120 and computing system 102. Supervisor device 140 may include or more input and/or output devices for monitoring interactions between user device 120 and computing system 102 and/or for interacting with computing system 102 and/or user device 120. For example, supervisor device 140 may include a display device (e.g., for displaying transcripts received from computing system 102 of the interactions between user device 120 and computing system 102 and/or for displaying alerts received from computing system 102), a keyboard, mouse, and/or microphone (e.g., for generating audio signals from utterances by human operator 110).

Health care provider system 142 may represent a computing system, such as a server, a desktop or laptop computer, a smartphone, a tablet computer, cloud-based system, or any other device associated with one or more health care providers (e.g., primary care physicians, specialists, or nurse practitioners). In some examples, health care provider system may store information about the one or more health care providers including health care provider types (e.g., primary care physicians, specialists, or nurse practitioners), schedules, experience, training, and/or specialties.

During operation, computing system 102 may receive a request for a medical appointment from user 119 through user device 120 (e.g., a request to establish a communication session between user device 120 and computing system 102). In some examples, user 119 may request the medical appointment via a user interface or smart voice assistant on user device 120. Computing system 102 may engage in a dialog with user 119 to schedule a medical appointment 132. During the dialog, computing system 102 may stream one or more requests 150 for audio input 130 to user device 120. User 119 may speak responses into user device 120, which communicates the responses as audio input 130 to computing system 102. In some examples, the dialog may resemble a phone conversation. In some examples, the dialog may resemble an interaction with a smart voice assistant. In some examples, the dialog may be in text, including in a chat or through a series of user interface forms. In some examples, human operator 110 may supervise the dialog between computing system 102 and user 119 on supervisor device 140. For example, computing system 102 may stream audio input 130 and requests 150 and/or a transcript of audio input 130 and requests 150 to supervisor device 140 in real time or near-real time. In some examples, human operator 110 may determine that user 119 may be experiencing a life threatening health condition (or any other emergency situation) and that user 119 should contact emergency services. In that case, human operator 110 may intervene in the dialog (e.g., automatically connect user 119 to emergency services, speak with user 119 directly). In some examples, computing device 102 transmits an alert to supervisor device 140 when certain conditions are met (e.g., when an emergency situation is detected), as described in further detail.

Computing system 102 may extract information from audio input 130 (including patient symptom information) and compare the extracted information to clinical guideline information to determine one or more probable health conditions of user 119. Additionally or alternatively, computing system 102 may compare/apply the guideline information to at least one of electronic health data associated with the user (e.g., patient medical history or previous interactions with the user when scheduling appointments or during the actual visits with the medical provider), epidemiological data, or local area data to determine one or more probable health conditions of user 119. Computing system 102 may determine a time allotment (e.g., a duration), identify a health care provider type (e.g., a primary care physician, a specialist, or a nurse practitioner) from health care provider system 142, and a platform (e.g., in-person consultation, video consultation, telephone consultation, chat consultation, email consultation) for a medical appointment 132 based on the one or more probable health conditions. In some examples, computing system 102 may identify a health care provider based on that providers schedule and/or skills or experience with the user's probable health condition. In some examples, computing system 102 may also determine one or more features about the user based on the extracted information and modify the time allotment for the medical appointment 132, the health care provider type, and/or platform based on the one or more features. In general, a feature about the user is one or more characteristics about the user or the user's speech. Features about the user may include the emotional state or emotional characteristic(s) of the user (e.g., whether the user is worried, nervous, confident, agitated, annoyed, or in any other emotional state), disfluencies (e.g., indications of confusion or an inability to understand medical terminology or conditions), whether the user is a non-native language speaker, the user's age, whether the user has a disability, a symptom that the user is experiencing, or any other characteristic about the user or the user's speech. Computing system 102 may output (e.g., transmit) medical appointment 132 to user device 120, health care provider system 142, and/or supervisor device 140. For example, computing system 102 may provide a suggested time slot (including date, time, and duration) for the medical appointment with the health care provider for the time allotment.

During the dialog, computing system 102 may determine whether it requires additional information from user 119 to schedule the appointment. For example, computing system 102 may compare extracted information from audio input 130 to clinical guideline information to and determine that additional information is required from user 119 to determine whether the user 119 is experiencing one or more other symptoms associated with a particular health condition. In response to determining that additional information in required, computing system 102 may output one or more requests 150 to user device 120 for the additional information. For example, the extracted information from audio input 130 may indicate that user 119 is experiencing a subset of symptoms for a particular medical condition found in a particular medical guideline, and computing system 102 may generate one or more requests 150 for audio input 130 regarding one or more of the remaining symptoms for the particular medical condition. In this way, computing system 102 may determine whether user 119 may be experiencing the particular medical condition to better determine the appropriate health care provider type, time allotment, and/or platform for the medical appointment.

As described herein, computing system 102 may process clinical guidelines to generate the guideline information that is compared to audio data 130. For example, computing system 102 may receive clinical guidelines in natural language text and/or flow charts as input, extract a plurality of guideline key phrases from the clinical guidelines, and normalize the plurality of guideline key phrases into normalized guideline expressions. In some examples, computing system 102 may identify the most relevant clinical guidelines (e.g., the most relevant guideline expressions) as the guideline information to compare to the extracted information of audio input 130. For example, computing system 102 may determine one or more clinical inferences (e.g., symptoms, potential medical conditions) based on the extracted information from audio input 130 and identify relevant clinical guidelines based on those clinical inferences (e.g., identify the guidelines associated with particular symptoms or potential medical conditions). In some examples, computing system 102 may rank the relevant clinical guidelines from the most relevant clinical guidelines to the least relevant clinical guidelines. Additionally or alternatively, computing system 102 may identify the most relevant clinical guideline based on health data (e.g., patient medical history), epidemiological data, or local area data. In this way, the computing system only uses the most relevant clinical guideline to determine the one or more potential medical conditions. In some examples, computing system 102 stores audio input 130 within the electronic health data associated with the user. In some examples, feedback information after the medical appointment may be entered into computing system 102 to improve the identification of relevant clinical guidelines, determination of potential medical conditions, and/or the time allotments for medical appointments. In this way, computing system 102 may schedule medical appointments with more accurate time allotments to better utilize medical personnel, properly diagnose patients, and reduce wait times.

Figure 2:
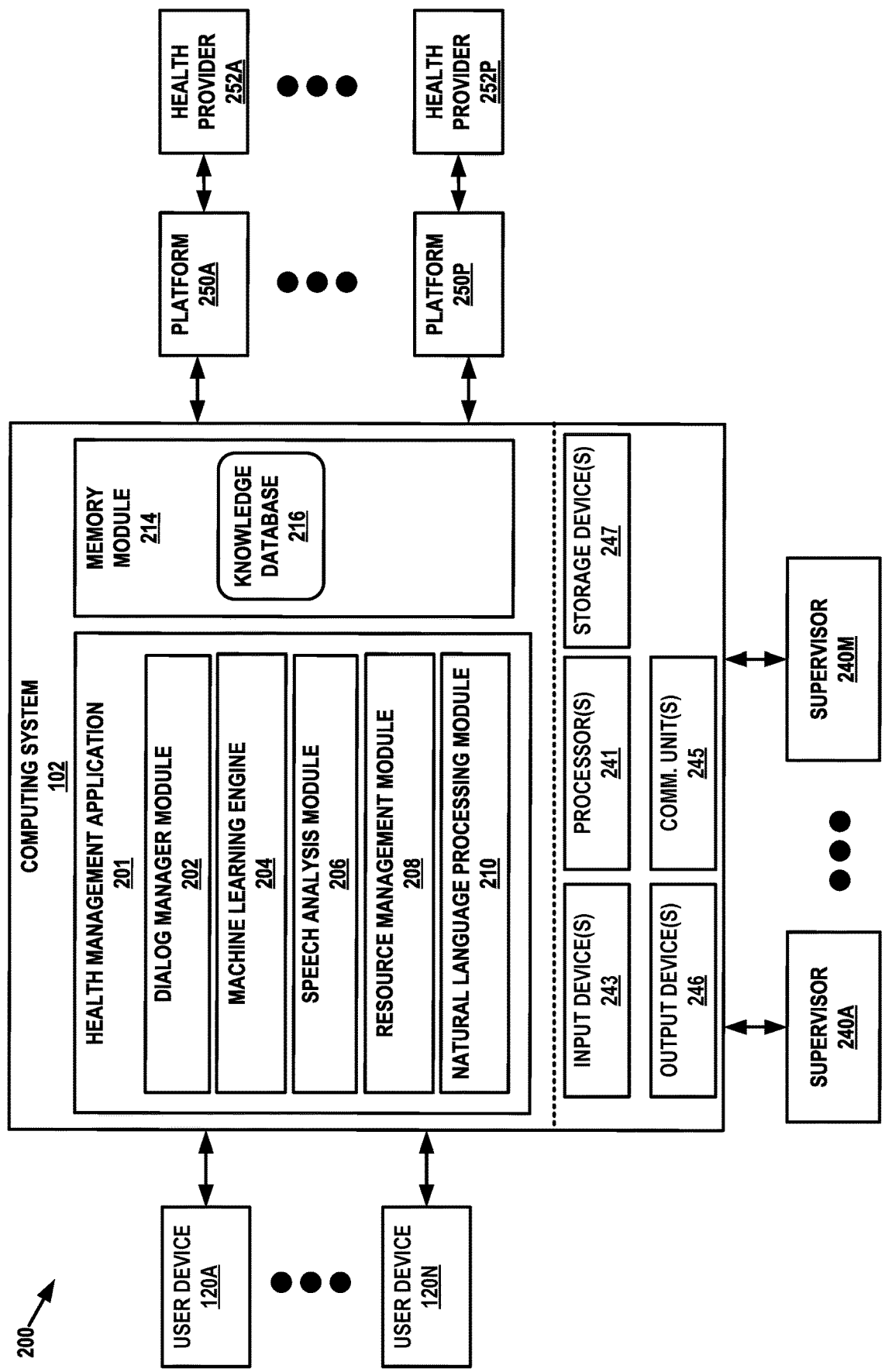
FIG. 2 is a block diagram illustrating an example health management system with an example instance of the computing system of FIG. 1, according to techniques of this disclosure.

FIG. 2 is a block diagram illustrating an example health management system 200 with an example instance of computing system 102 of FIG. 1, according to techniques of this disclosure.

Computing system 102 of FIG. 2 illustrates an example instance of computing system 102 of FIG. 1 in further detail. As described above with reference to FIG. 1, computing system 102 is capable of performing various functions of health management such as but not limited to dynamic resource management, identifying and obtaining missing data about and from a user. In some examples, computing system 102 connects patients (e.g., users 119 of FIG. 1), members of a health provider team (e.g., health providers 252A-252P), and supervisors 240A-240M (e.g., human operators or supervisors 110 of FIG. 1). For example, computing system 102 may establish a communication sessions with one of user devices 120A-120N and one of supervisor 240A-240M to schedule a medial appointment with any of heal care providers 252A-252N via any of communications platforms 250A-250P for each of the users associated with user devices 120A-120N. In some examples, supervisors 240A-240N may each correspond to a human operator 110 using a supervisor device 140 of FIG. 1. In some examples, platforms 250A-250B may correspond to a conceptual communications platform, including an in-person, video, telephonic, chat, and/or email communications platform. Each of health providers 252A-252P may correspond to a health care provider (e.g., a primary care physician, a specialist, or a nurse practitioner) or a computing device (e.g., desktop or laptop computer, a smartphone, a tablet computer) associated with the health care provider. In some examples, computing system 102 may establish a communication session between one or user devices 120A-120N and one or health provider 252A-252P over one of platform 250A-250P (e.g., for a medical appointment).

In this example, computing system 102 includes one or more input devices 243, one or more processors 241, one or more output devices 246, one or more storage devices 247, and one or more communication units 245. One or more of the devices, modules, storage areas, or other components of computing system 102 may be interconnected to enable inter-component communications (physically, communicatively, and/or operatively). In some examples, such connectivity may be provided through communication channels, a system bus, a network connection, an inter-process communication data structure, or any other method for communicating data.

One or more processors 241 of computing system 102 may implement functionality and/or execute instructions associated with computing system 102 or associated with one or more modules illustrated herein and/or described below. One or more processors 241 may be, may be part of, and/or may include processing circuitry that performs operations in accordance with one or more aspects of the present disclosure. Examples of processors 241 include microprocessors, application processors, display controllers, auxiliary processors, one or more sensor hubs, and any other hardware configured to function as a processor, a processing unit, or a processing device. Computing system 102 may use one or more processors 241 to perform operations in accordance with one or more aspects of the present disclosure using software, hardware, firmware, or a mixture of hardware, software, and firmware residing in and/or executing at computing system 102.

One or more communication units 245 of computing system 102 may communicate with devices (e.g., user devices 120, supervisor device 140, supervisors 240A-240M, health providers 252A-252P, health care provider system 142) external to computing system 102 by transmitting and/or receiving data, and may operate, in some respects, as both an input device and an output device. In some examples, communication unit 245 may communicate with other devices over a network. In other examples, communication units 245 may send and/or receive radio signals on a radio network such as a cellular radio network. In other examples, communication units 245 of computing system 102 may transmit and/or receive satellite signals on a satellite network such as a Global Positioning System (GPS) network. Examples of communication units 245 include a network interface card (e.g. such as an Ethernet card), an optical transceiver, a radio frequency transceiver, a GPS receiver, or any other type of device that can send and/or receive information. Other examples of communication units 245 may include devices capable of communicating over Bluetooth®, GPS, NFC, ZigBee, and cellular networks (e.g., 3G, 4G, 5G), and Wi-Fi® radios found in mobile devices as well as Universal Serial Bus (USB) controllers and the like. Such communications may adhere to, implement, or abide by appropriate protocols, including Transmission Control Protocol/Internet Protocol (TCP/IP), Ethernet, Bluetooth, NFC, or other technologies or protocols.

One or more input devices 243 may represent any input devices of computing system 102 not otherwise separately described herein. One or more input devices 243 may generate, receive, and/or process input from any type of device capable of detecting input from a human or machine. For example, one or more input devices 243 may generate, receive, and/or process input in the form of electrical, physical, audio, image, and/or visual input (e.g., peripheral device, keyboard, microphone, camera).

One or more output devices 246 may represent any output devices of computing system 102 not otherwise separately described herein. One or more output devices 246 may generate, receive, and/or process input from any type of device capable of detecting input from a human or machine. For example, one or more output devices 246 may generate, receive, and/or process output in the form of electrical and/or physical output (e.g., peripheral device, actuator).

One or more storage devices 247 within computing system 102 may store information for processing during operation of computing system 102. Storage devices 247 may store program instructions and/or data associated with one or more of the modules described in accordance with one or more aspects of this disclosure. One or more processors 241 and one or more storage devices 247 may provide an operating environment or platform for such modules, which may be implemented as software, but may in some examples include any combination of hardware, firmware, and software. One or more processors 241 may execute instructions and one or more storage devices 247 may store instructions and/or data of one or more modules. The combination of processors 241 and storage devices 247 may retrieve, store, and/or execute the instructions and/or data of one or more applications, modules, or software. Processors 241 and/or storage devices 247 may also be operably coupled to one or more other software and/or hardware components, including, but not limited to, one or more of the components of computing system 102 and/or one or more devices or systems illustrated as being connected to computing system 102.

In some examples, one or more storage devices 247 are temporary memories, meaning that a primary purpose of the one or more storage devices is not long-term storage. Storage devices 247 of computing system 102 may be configured for short-term storage of information as volatile memory and therefore not retain stored contents if deactivated. Examples of volatile memories include random access memories (RAM), dynamic random-access memories (DRAM), static random-access memories (SRAM), and other forms of volatile memories known in the art. Storage devices 320, in some examples, also include one or more computer-readable storage media. Storage devices 320 may be configured to store larger amounts of information than volatile memory. Storage devices 320 may further be configured for long-term storage of information as non-volatile memory space and retain information after activate/off cycles. Examples of non-volatile memories include magnetic hard disks, optical discs, Flash memories, or forms of electrically programmable memories (EPROM) or electrically erasable and programmable (EEPROM) memories.

Health management application 201 in the example of FIG. 2 includes dialog manager module 202, machine learning engine 204, speech analysis module 206, resource management module 208, and natural language processing module 210. Computing system 102 may also include a memory module 214 and knowledge database 216. In some examples, memory module 214 and/or knowledge database 216 may be separate from computing system. For example, memory module 214 and/or knowledge database 216 may comprise remote server, cloud, database, or other storage. Memory module 214 may be one of storage devices 247 in some cases. Likewise, any of dialog manager module 202, machine learning engine 204, speech analysis module 206, resource management module 208, and natural language processing module 210 may be a cloud or other remote service.

Dialog manager module 202 may manage communications sessions between user devices 120, supervisors 240, health care providers 252, and computing system 102. For example, dialog manager module 202 may receive, via one or more communication units 245, a request for a medical appointment from a user device 120 and establish a communications session between user device 120 and computing system 102. In some examples, dialog manager module 202 may also establish a communications session with supervisor 240 or supervisor device 140 such that a supervisor or human operator may supervise the dialog between computing device 102 and user device 120. In some examples, dialog manager module 202 enables a one-on-one communicating session between any of user devices 120 and any of supervisor devices 240 or a one-to-many communication session (e.g., a plurality of communication sessions) between a supervisor device 240 and many users to supervise interactions between users and computing system 102. For example, dialog manager module 202 may output for display a transcription of dialogs between one or more users and computing system 102 to supervisor device 140. Dialog manager module 202 may also output for display a status of the one or more dialogs and may alert supervisor 240 when certain conditions are met, as described below with reference to FIG. 4.

Dialog manager module 202 may output one or more requests for information (e.g., requests 150 of FIG. 1) to user device 120. For example, dialog manager module 202 may request identification information to verify the identity of the user, to obtain electronic health data corresponding to the user (e.g., medical history information), and/or to obtain information about the purpose for the request for a medical appointment. Dialog manager module 202 may receive, via one or more communication units 245, audio input (e.g., audio input 130 of FIG. 1) in response to the one or more requests for information. In some examples, dialog manager module 202 may base at least some of the one or more requests for information based on the audio input. For example, the user may complain of a sore throat (e.g., in audio input 130) and dialog manager module 202 may output one or more of the following requests to determine whether strep throat (or any other health condition associated with a sore throat) is a probable health condition for the user: "Do you have a fever?"; "Are you experiencing nausea?", "Have you been vomiting?"; and/or "Do you have swollen or tender lymph nodes in your neck?". In some examples, the dialog including the requests from dialog manager module 202 and the audio input from the user device may resemble a phone conversation. In some examples, the dialog may resemble an interaction with a smart voice assistant. In some examples, the dialog may be in text, including in a chat or through a series of user interface forms. In some examples, the symptoms, requests, or rules to determine whether the user is experiencing particular health conditions may be stored in knowledge database 216 and/or memory module 214.

Speech analysis module 206 may analyze the audio input received from user device 120. For example, speech analysis mode 206 may perform speech recognition on the audio input and transcribe the audio input into text. In some examples, machine learning engine 204 applies a machine learning (ML) model (e.g., a Hidden Markov Model or neural networks) trained to recognize speech in the audio input. In some examples, speech analysis mode 206 may transmit, via one or more communication units 245, the transcription of the audio input to one or more supervisors 240. In some examples, speech analysis module 206 may comprise any commercial off-the-shelf or open-source speech analysis, audio processing, and/or language analysis software, such as Automatic Requirements Specification Extraction from Natural Language (ARSENAL), Very Agile Language Extraction Toolkit (VALET), and/or SenSay Analytics™. In some examples, speech analysis module 206 applies audio processing software to audio input 130 to produce text input. Speech analysis module 206 may then apply ARSENAL or VALET to text generated from audio input 130 to produce machine understandable specifications, formulas, models, or expressions. Speech analysis module 206 may also apply SenSay Analytics™ to perform speaker state classifications from audio input 130, including emotion (e.g., emotional state), sentiment, cognition, health, mental health and communication quality.

Machine learning engine 204 may include one or more neural networks, such as one or more of a Deep Neural Network (DNN) model, Recurrent Neural Network (RNN) model, and/or a Long Short-Term Memory (LSTM) model. In general, DNNs and RNNs learn from data available as feature vectors, and LSTMs learn from sequential data.

Machine learning engine 204 apply other types of machine learning to train any of the ML models described herein. For example, machine learning engine 204 may apply one or more of nearest neighbor, naïve Bayes, decision trees, linear regression, support vector machines, neural networks, k-Means clustering, Q-learning, temporal difference, deep adversarial networks, or other supervised, unsupervised, semi-supervised, or reinforcement learning algorithms to train ML models.

Natural language processing module 210 performs functions to understand human language. For example, natural language processing module 210 may analyze and extract information (including patient symptom information) from the speech recognized (and/or transcribed) by speech analysis module 206. That is, natural language processing module 210 will analyze audio input 130 received in response to requests 150 of FIG. 1. For example, computing system 102 may output the request "Do you have a fever?" to user device 120, receive "I have had a temperature of 104 for since yesterday" or "Yes, for two days" in response, and determine that the user has had a fever for about 48 hours based on audio input 130 received from user device 120 and in the context of the one or more requests outputted to the user device 120. In some examples, natural language processing module 210 may execute a commercial off-the-shelf or open-source speech analysis, audio processing, and/or language analysis software, including ARSENAL, VALET, and/or SenSay Analytics™.

In some examples, health management application 201 may further extract information from non-verbal (non-speech) portions of audio input 130 (including patient symptom information). For example, health management application 201 may detect coughing (including whether the cough is dry or productive), wheezing, shortness of breath, sneezing, congestion, sniffling, or any other non-verbal indications of probable symptoms of potential health conditions. Health management application 201 may further extract the emotional state or characteristics of the user. For example, health management application 201 may determine whether the user is worried, nervous, confident, agitated, annoyed, or in any other emotional state. For example, machine learning engine 204 may apply one or more ML models trained to extract the emotional state of the user from the audio input. These one or more ML models may be stored in knowledge database 216 and/or memory module 214. Further example details of extracting information from audio input can be found in U.S. patent application Ser. No. 15/179,816, filed Jun. 10, 2016 and entitled "REAL-TIME SPEAKER STATE ANALYTICS PLATFORM," the entire contents of which is incorporated by reference in its entirety.

Health management application 201 may compare or match the extracted information from audio data 130 to guideline information stored in knowledge database 216 and/or memory module 214. In some examples, guideline information may comprise rules or expressions of symptoms that may be present when a patient is experiencing a particular health condition. In some examples, guideline information may comprise one or more ML models trained to detect whether a user is experiencing particular health conditions. For example, health management application 201 may determine whether a user is experiencing one or more potential health conditions by applying the guideline information (e.g., rules, expressions, or ML models) to the extracted information from audio input 130. For example, the user may be experiencing health condition C (e.g., strep throat) if conditions (or symptoms) X (e.g., sore throat), Y (e.g., nausea or vomiting), and Z (e.g., swollen or tender lymph nodes) are present.

In some examples, health management application 201 may identify the most relevant clinical guidelines (e.g., the most relevant guideline expressions) as the guideline information to compare to the extracted information of the audio input. For example, the user may complain about X (e.g., sore throat) and health management application 201 may identify clinical guidelines related to the common cold, flu, strep throat, laryngitis, glandular fever, and/or tonsillitis. In some examples, health management system 201 may identify the most relevant clinical guideline based on electronic health data corresponding to the user (e.g., patient medical history), epidemiological data, or data about health conditions present the local area corresponding to the user's location (or previously visited locations) (e.g., without considering the audio input or responses from the user). Either way, health management application 201 may compare the extracted information from audio data 120 (e.g., extracted symptom information) to the guideline information from these relevant guidelines. In some examples, health management application 201 may rank the most relevant clinical guidelines to compare to the extracted information of the audio input. For example, health management application 201 may rank the relevant clinical guidelines based on the number of conditions or symptoms matched for each health condition associated with each clinical guideline. In this way, the computing system only uses the most relevant clinical guideline to determine probable health conditions or one or more clinical inferences.

In some examples, health management application 201 may determine that additional information is necessary to determine whether the user is experiencing one or more other conditions or symptoms corresponding to the potential health conditions associated with these relevant guidelines and dialog manager module 202 may formulate one or more requests (e.g., requests 150 of FIG. 1) for the additional information to determine whether those additional conditions or symptoms are present. In some examples, health management application 201 stores audio input 130, transcript, and/or extracted information within the electronic health data associated with the user in knowledge database 216 and/or memory module 214.

Resource management module 208 performs functions to schedule medical appointments 132 of FIG. 1. For example, resource management module 208 may determine a time allotment (e.g., a duration), identify a health care provider type (e.g., identify a primary care physician, a specialist, or a nurse practitioner from health providers 252A-252P) and a platform from platforms 250A-250P (e.g., in-person consultation, video consultation, telephone consultation, chat consultation, email consultation) for a medical appointment based on the one or more probable health conditions determined by health management application 201. In some examples, resource management module 208 may identify a particular health care provider based on that providers schedule and/or skills or experience with the user's probable health condition. In some examples, each probable health condition may have a particular time allotment associated with it. For example, a cold may have a ten-minute time allotment, diabetes may have a fifteen-minute time allotment, and lymphoma may have a thirty-minute time allotment. In some examples, these time allotment and probable health condition associations may be stored in knowledge database 216 and/or memory module 214. For example, the time allotments may be stored in one or more look up tables in knowledge database 216 and/or memory module 214 that are indexed by the associated health condition. In some examples, the health management application 201 may also determine one or more features about the user based on the extracted information and modify the time allotment for the medical appointment 132, the health care provider type, and/or platform based on the one or more features. Resource management module 208 may output (e.g., transmit via one or more communication units 245) medical appointment 132 to user device 120, health care provider system 142, and/or supervisor device 140. To output medical appointment 132, resource management module 208 may generate a user interface that indicates medical appointment 132 for display at user device 120 or generate audio data that indicates medical appointment 132 for output at user device 120, for example.

For example, computing system 102 may provide a suggested time slot for the medical appointment with one of health provider 252A-252P via one of platform 250A-250P for the time allotment. In some examples, feedback information may be entered into the computing system 102 (e.g., by a human operator or health provider) after the medical appointment to improve estimated time allotments, the identification of relevant clinical guidelines, and/or the identification of potential health conditions. In this way, computing system 102 may schedule medical appointments with more accurate time allotments to better utilize medical personnel, properly diagnose patients, and reduce wait times.

In some examples, natural language processing module 210 may also process clinical guidelines to generate the guideline information. For example, computing system 102 may receive clinical guidelines in the form natural language text and/or flow charts as input, and natural language processing module 210 may extract a plurality of guideline key phrases from the clinical guidelines and normalize the plurality of guideline key phrases into normalized guideline expressions (e.g., by recognizing relationships between the key phrases). These normalized guideline expressions may comprise the guideline information that is compared to the extracted information from audio input 130. An example normalized expression may comprise "X+Y+Z→C", where X represents sore throat, Y represents nausea or vomiting, Z represents swollen or tender lymph nodes, and C is strep throat.

Figure 3:
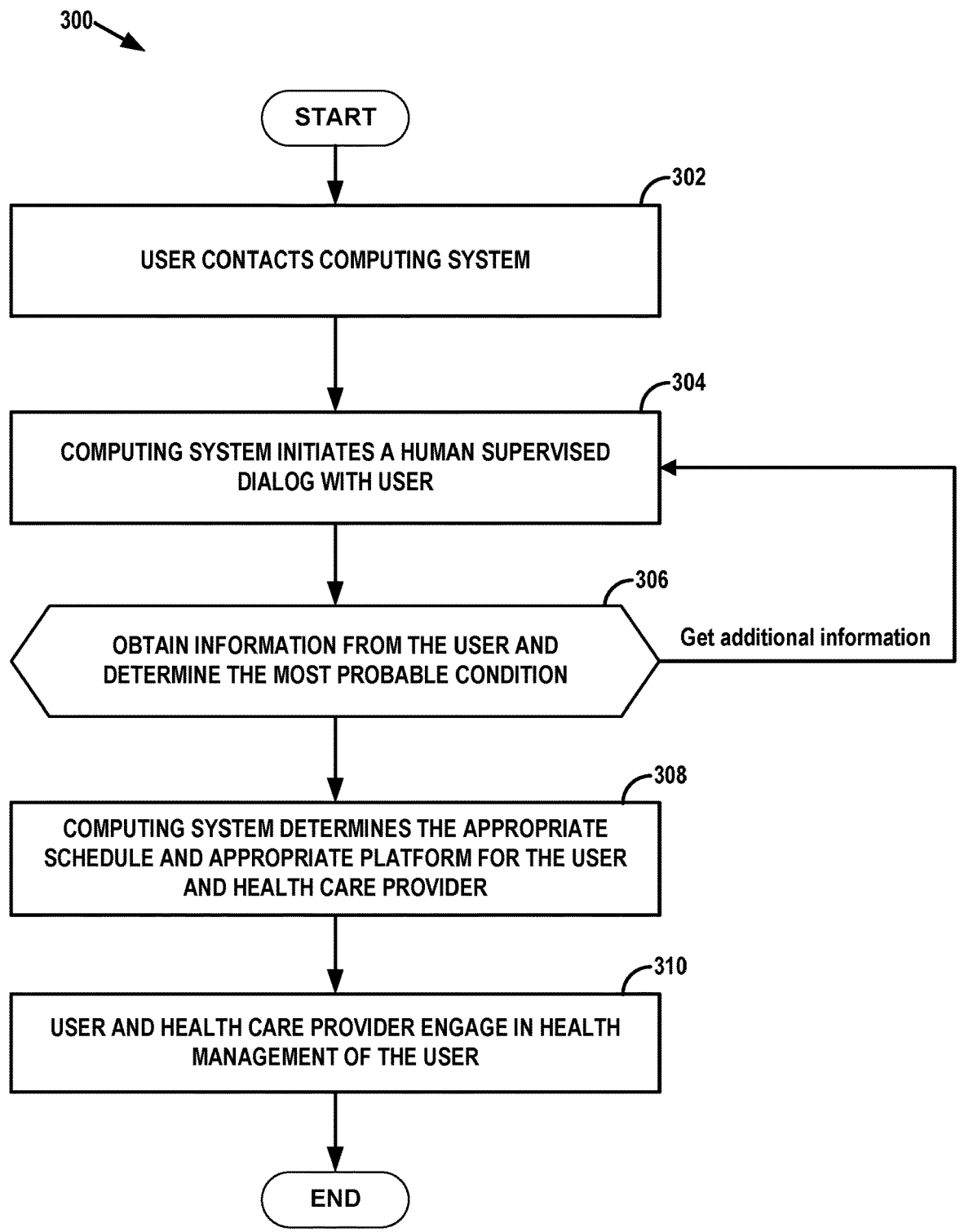
FIG. 3 is a flowchart illustrating example operations of a method for determining a time allotment, health care provider type, and/or platform for a medical appointment, according to techniques of this disclosure.

FIG. 3 is flowchart 300 illustrating example operations of a method for determining a time allotment, health care provider type, and/or platform for a medical appointment, according to techniques of this disclosure. In some examples, one or more operations shown in FIG. 3 may be performed by computing system 102.

Initially, user 119 contacts computing system 102 with user device 120 (302). For example, user 119 may call computing system 102 with user device 120 to request a medical appointment. In response to receiving the request (e.g., the phone call), computing system 102 may initiates a human supervised dialog with user 119 (304). For example, computing system 102 may establish a communication session between user device 120, supervisor device 140, and computing system 102, in which computing system 102 engages in a dialog with user 112 (e.g., via user device 120) while supervisor 110 (or human operator) supervises the dialog (e.g., via supervisor device 140). In some examples, computing system 102 transmit an audio stream and/or transcript from the dialog between user 119 and computing system 102 to supervisor device 140 in real-time or near real-time.

Computing system 102 obtains information from user 119 and determines the most probable health condition that user 119 is experiencing. For example, user 119 may complain about a sore throat and identify clinical guidelines related to probable health conditions associated with a sore throat, including the common cold, flu, strep throat, laryngitis, glandular fever, and/or tonsillitis. Computing system 102 may then output one or more requests for information to user device 120 to determine whether user 119 may be experiencing the common cold, flu, strep throat, laryngitis, glandular fever, and/or tonsillitis. In some examples, depending on the assessment by the human supervisor, the information about the patient's probable health condition is passed along within computing system 102 for it to determine if additional information needs to be obtained from user 119. In some examples, the human supervisor may determine that user 119 should call emergency services and the informant about the probable health condition is not passed within computing system 102. For example, the human supervisor may intervene and instruct user 119 to call emergency services and/or connect user 119 to emergency services. If additional information is needed ("get additional information" branch of 306), computing system 102 continues to engage with the patient through the human supervised dialog system (306). After the information has been gathered, computing system 102 determines the appropriate schedule including the appropriate amount of time required to manage the patient (e.g., time allotment for medical appointment based on the probable health condition(s)), the appropriate health care provider (e.g., primary care physician, nurse practitioner, or other resource) and the appropriate platform (e.g., face to face visit, phone engagement or other resource) (308). After this determination, the patient and the health care provider then may engage in health management of user 119 (e.g., conduct the medical appointment) (310). In some examples, computing system 102 establishes a communication session for the medical appointment. In some examples, feedback information after the medical appointment may be entered into computing system 102 to improve the identification of relevant clinical guidelines, determination of potential medical conditions, and/or the time allotments for medical appointments. In some examples, computing system 102 stores audio input 130 within the electronic health data associated with user 119.

Figure 4:
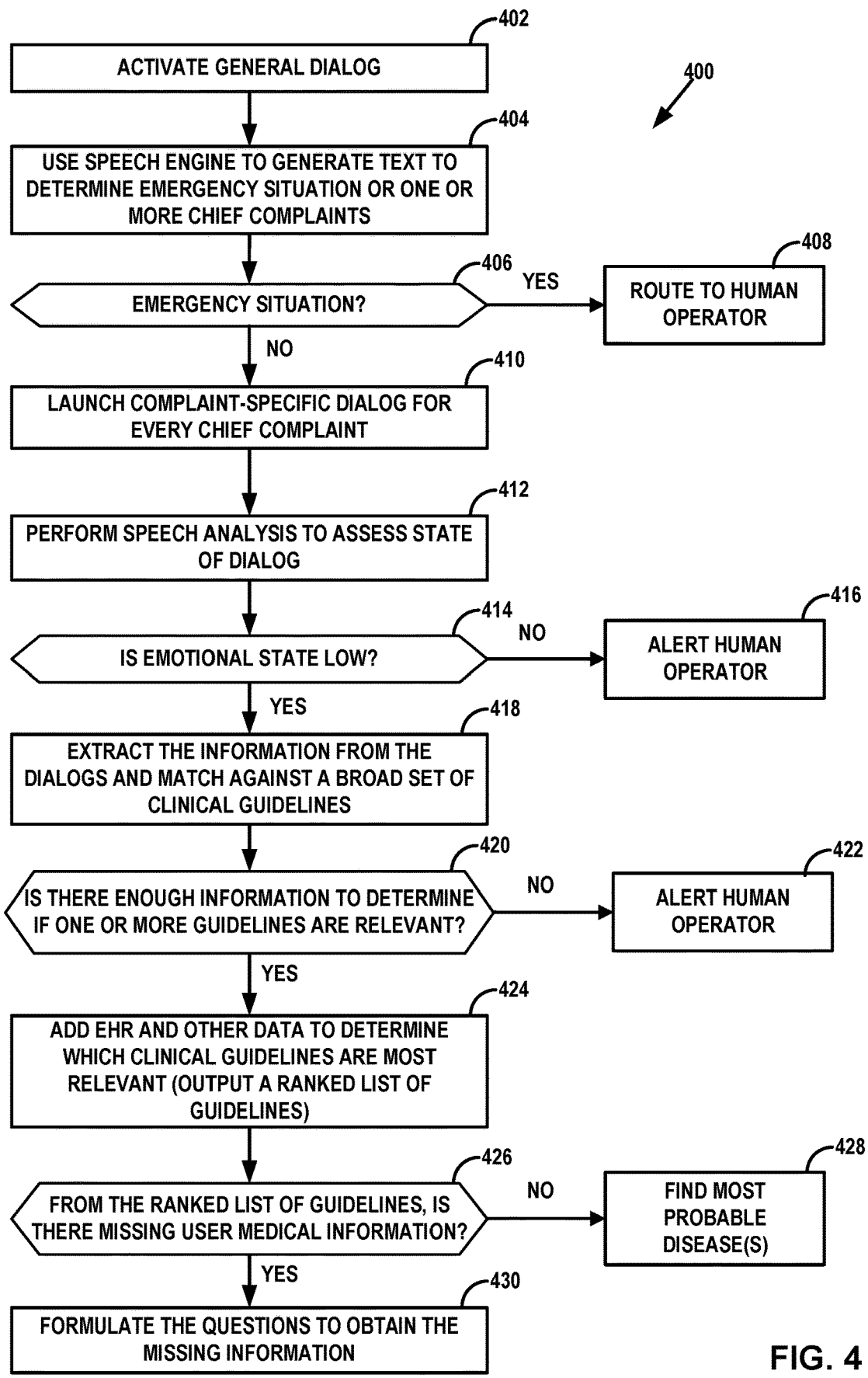
FIG. 4 is a flowchart illustrating example operations of a method for obtaining medical information from a user, according to techniques of this disclosure.

FIG. 4 is a flowchart 400 illustrating example operations of a method for obtaining medical information from a user, according to techniques of this disclosure. In some examples, one or more operations shown in FIG. 3 may be performed by computing system 102.

Computing system 102 activates a general dialog between user 119 and computing system 102 in response to user 119 contacting computing system 102 or computing system 102 contacting user 119 (402). This general dialog may include questions for the name and other identifying data of user 119 for user verification. After user 119 has been verified, computing system 102 may ask standard questions such as "What can I help you with?". Computing system 102 then analyzes the user's responses (e.g., audio input 130). For example, speech analysis module 206 and/or natural language processing module 210 may determine if an emergency situation exists (e.g., if user 119 is experiencing a life threating health condition) (406). If such an emergency situation exists (YES branch of 406), computing system 102 automatically routes the communication session to a human operator (e.g., to medical or emergency services personnel) (408). If computing system 102 determines that an emergency situation does not exist (NO branch of 406), computing system 102 launches a complaint-specific dialog for each chief complaint by user 119. For example, a complaint may comprise an indication of a symptom (e.g., sore throat, chest pain, night sweats) or a request to be checked out for a probable health condition (e.g., diabetes, cancer, strep throat, arthritis). Computing system 102 may identify one or more relevant clinical guidelines associated with each complaint. For example, computing system 102 may identify all the clinical guidelines associated with each complaint/symptom.

Following the identification of the chief complaints, computing system 102 may launch multiple complaint-specific dialogs in succession (410). For example, if user 119 indicated that he or she has a fever and an earache, two complaint-specific dialogs may be initiated, one to obtain more information about the fever (e.g., "How high is the fever?", "When did the fever start?", "Do you have a cold?", etc.) and another to obtain more information about the earache (e.g., "Do you have pain in both ears or in one ear?", "When did the pain start?", etc.). In some examples, computing system 102 pay conduct the two complaint-specific dialogs serially or may combine them. Either way, computing system 102 ensures to obtain information related to both dialogs. Computing system 102 may also be continually assessing the emotional state or characteristics of user 119 (412) in parallel to these ongoing dialogs between user 119 and computing system 102. While this step (412) appears subsequent to the launching of the dialogs (410), these steps may be performed in parallel or concurrently. If an emotional characteristic or state is lower than a threshold value (NO branch of 414), computing system 102 may alert a human operator (416). The emotional state of user 119 may be low if he or she is worried, depressed, confused, etc. In some examples, computing system 102 may alert a human operator if the emotional state of user 119 is higher than a threshold value. The emotional state of user 119 may be high if he or she is agitated, angry, stressed, etc. In some examples, other characteristics may be determined in additional to emotional state. While the emotional state or level is being assessed, computing system 102 continues to obtain the information and extracts information from these dialogs (e.g., from audio input 130) and matches the extracted information against a broad set of clinical guidelines to identify one or more relevant clinical guidelines (418) (e.g., as described in further detail below with reference to FIG. 5).

Computing system 102 may determine whether it has sufficient information to identify one or more relevant guidelines (420). For example, computing system 102 may determine a number of matches between the extracted information and a particular clinical guideline (e.g., matching one or more conditions or symptoms that are outline in the particular clinical guideline). If computing system 102 determines that no clinical guideline was matched over a threshold (NO branch of 420), computing system 102 determines that not enough information that additional information from the user is required and, optionally, alerts a human operator to help obtain more information (422).

If computing system 102 determines that enough information to identify at least one relevant clinical guideline (YES branch of 420), computing system 102 may consider data from other sources such as the Electronic Health Record (EHR) associated with user 110 (e.g., patient medical record), epidemiological data, data about prevalent conditions in the local area etc., to identify and/or rank clinical guidelines (424). For example, computing system 102 may identify guidelines that are associated with health conditions in the EHR (including health conditions in family history), epidemiological data, and/or the local area corresponding to the user's location (or previously visited locations). In some examples, computing system 102 may rank these guidelines based on the number of matches of conditions or symptoms identified in the guidelines when compared to the extracted information from audio input 130. From this ranked list of guidelines, computing system 102 determines if more information is needed from the patient ("missing information") (426). For example, computing system 102 may determine whether it has sufficient information to determine whether user 119 is experiencing one or more symptoms or conditions outlined in a particular guideline. In response to a determination that more information is needed from user 119 (YES branch of 426), computing system 102 formulates questions or requests to obtain the missing information from user 119. To achieve this, for each guideline, the concepts, symptoms, or conditions that are not matched may form the basis of a new set of questions. In some examples, computing system 102 may consider each ranked guideline in turn and collect information about the concepts, symptoms, or conditions that are not matched for a particular guideline. For example, computing system 102 may turn these concepts, symptoms, or conditions into questions. Subsequently a speech synthesizer module may then present these questions to the patient (e.g., output those questions to user device 120). This cycle may repeat for each ranked guideline until computing system 102 has sufficient information to determine whether the user is experiencing the particular health condition associated with each guideline. In response to a determination that computing system 102 has sufficient information (e.g., NO branch of 426), computing system 102 finds the most probable health condition (428). For example, computing system 102 may identify the one or more guidelines with the most number matches to the conditions or symptoms outlined in the guidelines when compared to the extracted information from audio input 130 as the most probable health condition(s). For example, computing system 102 may identify a number N (e.g., 1, 3, 5) of guidelines with the greatest number of symptoms that user 119 is experiencing as the most probable health condition(s). In some examples, computing system 102 identifies the health conditions associated with the ranked list of relevant guidelines as the most probable health conditions in raking order, with the heath condition associated with the highest ranked guideline as the most probable health condition and the health condition associated with the lowest ranked guideline as the least probable health condition.

Figure 5:
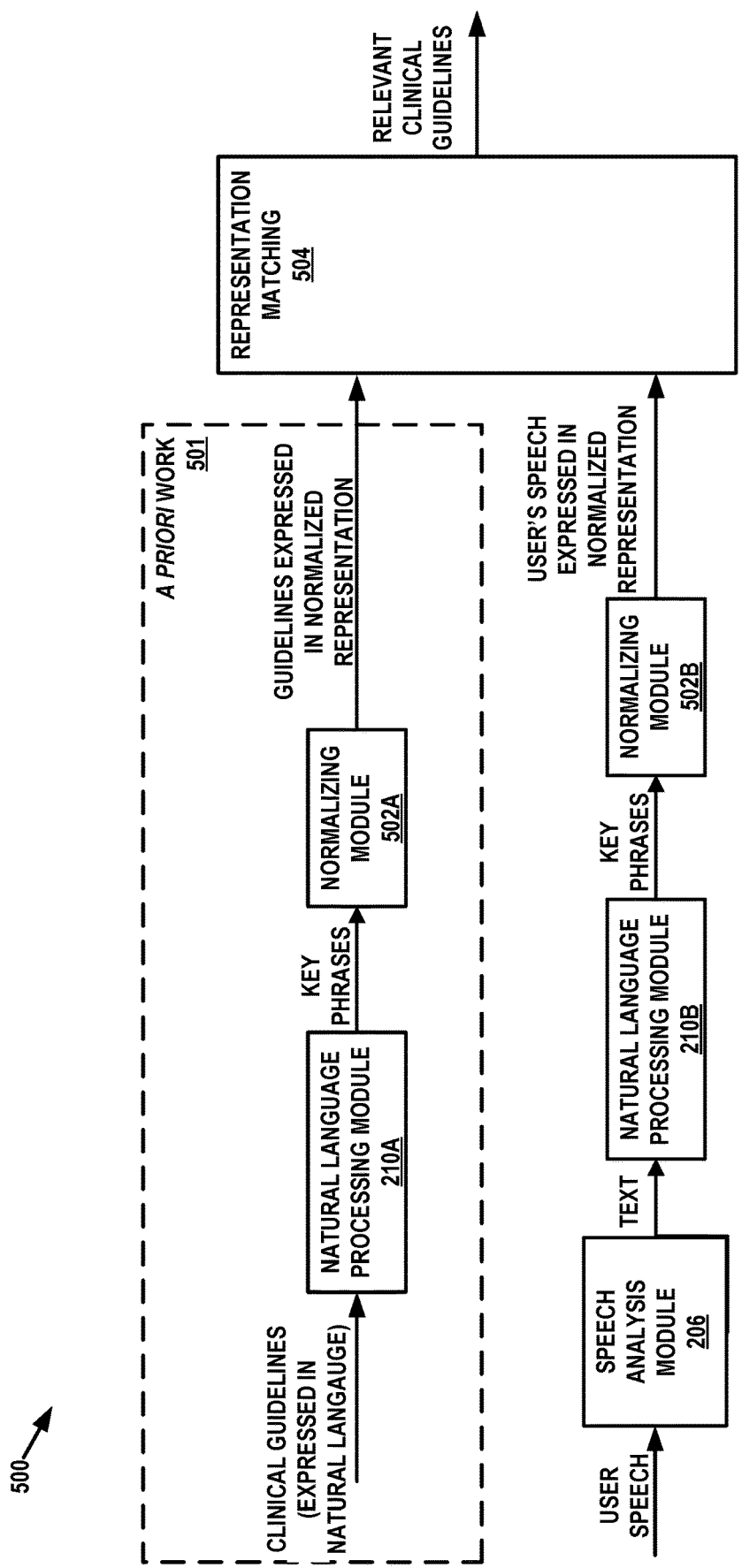
FIG. 5 is a conceptual diagram for identifying relevant clinical guidelines, according to techniques described herein.

FIG. 5 is a conceptual diagram 500 for identifying relevant clinical guidelines, according to techniques described herein. Diagram 500 is one example of the functions performed by computing system 102 at element 418 of flowchart 400 in FIG. 4

As shown in FIG. 5, computing system 102 may convert clinical guidelines, written in natural language, to a normalized representation of the guidelines in a priori work 501. For example, computing system 102 processes clinical guidelines to form rules or expressions that are used to determine whether a user is experiencing the particular health condition associated with each guideline. To achieve this, the clinical guidelines are input into the natural language processing module 210A which extracts key phrases from the natural language guidelines. In some examples, the clinical guidelines comprise flowcharts and natural language processing module 210A extracts key phrases from the flowchart elements. Either way, these extracted key phrases may then be input into normalizing module 502A that matches the key phrases to "normalized phrases" or expressions that describe the guideline (e.g., "X+Y+Z->C" as described above with reference to FIG. 2). In some examples, normalizing module 502A uses one or more ontologies to normalize the key phrases. For example, the utility Snomed Clinical Terms or other ontologies may be used. Thus, through the use of one these utilities, the guidelines may be represented by a normalized representation or expression. In some examples, the normalized representation may be in a language (except that standard or normalized phrases are used) or in some other machine recognizable representation. For example, a pain related guideline may be represented by a set of alphanumeric characters that represent an established code of some type. Thus, the clinical guidelines represented after normalization may be stored in memory of computing system 102 (e.g., in knowledge database 216 and/or memory module 214 of FIG. 2). In addition, this work may be performed apriori. In some examples, computing system 102 may normalize guidelines at element 418 of flowchart 400 in FIG. 4. In some examples, computing system 102 may normalize guidelines outside of flowchart 400 in FIG. 4 (e.g., not during a dialog between user 119 and computing system 102).

As shown in FIG. 5, user speech (or text), may also be converted into a normalized representation by computing system 102. For example, speech analysis module 206 may convert the speech of a patient (e.g., audio input 130 of FIG. 1) to text. Subsequently, natural language module 210B may extract key phrases from the text which are then normalized in by normalizing module 502B, as described above. Once the patient's speech is expressed in a normalized representation, computing system 102 may compare and match the normalized representation of user's speech (e.g., the output of normalizing module 502B) to the normalized representation of each of clinical guidelines stored in memory (e.g., the output of normalizing module 502A for each guideline) (504). As described above with reference to FIG. 2, a normalized representation for a clinical guideline may be "X+Y+Z->C", where X represents sore throat, Y represents nausea or vomiting, Z represents swollen or tender lymph nodes, and C is strep throat. A normalized representation of a user's speech may be "X+Y+R", where X represents sore throat, Y represents nausea, and R represents runny nose. When comparing these two exemplary normalized expressions, computing system 102 finds two matches (e.g., for X and Y). In some examples, computing system 102 may find one or more matches within one or more guidelines. In some examples, computing system 102 may identify each guideline with one or more matches as a relevant guideline. In some examples, computing system 102 may only identify the guidelines with matches above a threshold level (e.g. 2, 3, 5, or any number of matches) may be identified as relevant. In some examples, the threshold level may be percentage of conditions/symptoms matched (e.g., 25%, 30%, 50%). In some examples, the threshold level may be set (e.g., by a human operator, administrator or supervisor) to improve the matching result. In this way, computing system 102 may identify a broad set of guidelines that are applicable to the user's probable condition. In some examples, computing system 102 may rank the relevant guidelines based on the number of matches, where the guidelines with the higher number of matches is ranked higher than the guidelines with the lower number of marches (e.g., in descending order of matches). In some examples, representation matching 504 may be performed by health management application 201.

Figure 6:
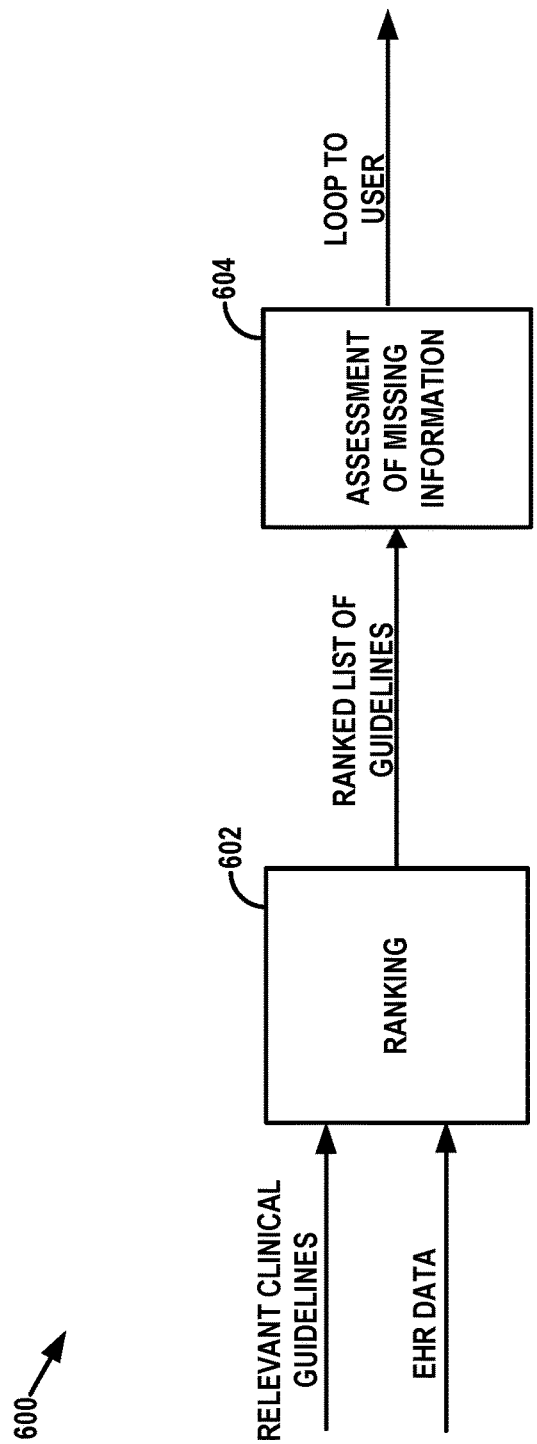
FIG. 6 is a conceptual diagram for ranking relevant clinical guidelines and identifying missing information to obtain from a user, according to techniques described herein.

FIG. 6 is a conceptual diagram 600 for ranking relevant clinical guidelines and identifying missing information to obtain from a user, according to techniques described herein. Diagram 600 is one example of the functions performed by computing system 102 at elements 424 and/or 430 of flowchart 400 in FIG. 4

As shown in FIG. 6, computing system 102 may rank relevant guidelines using data from one or more sources (602). In this example, computing system 102 ranks relevant guidelines using EHR data associated with the user (which may include audio input or text from one or more prior interactions or dialogs with computing system 102). In some examples, other data may be used, such as epidemiological data and/or data about prevalent conditions in the local area corresponding to the user (e.g., the user's location or previously visited locations). In some examples, the data from these various sources may be normalized. To rank the guidelines, computing system 102 may match normalized guideline expressions to normalized expressions of the EHR or other data rank relevant guidelines based on the number of matches where the guidelines with the higher number of matches to the EHR data are ranked higher than the guidelines with the lower number of marches to the HER data. Thus, the guideline with the greatest number of matches may be associated with the first rank with the guideline with the second most matches associated with the second rank. This process may be continued until the guideline with the least number of matches is found.

From the ranked list of relevant guidelines, computing device 102 may assesses whether any information related to the relevant clinical guidelines is missing (604). For example, computing system 102 may determine whether it has sufficient information to determine whether user 119 is experiencing one or more symptoms or conditions outlined in each of the ranked list of relevant guidelines. If so, computing system 102 formulates questions or requests to obtain the missing information from user 119 (e.g., as described above with reference to FIG. 4).

Figure 7:
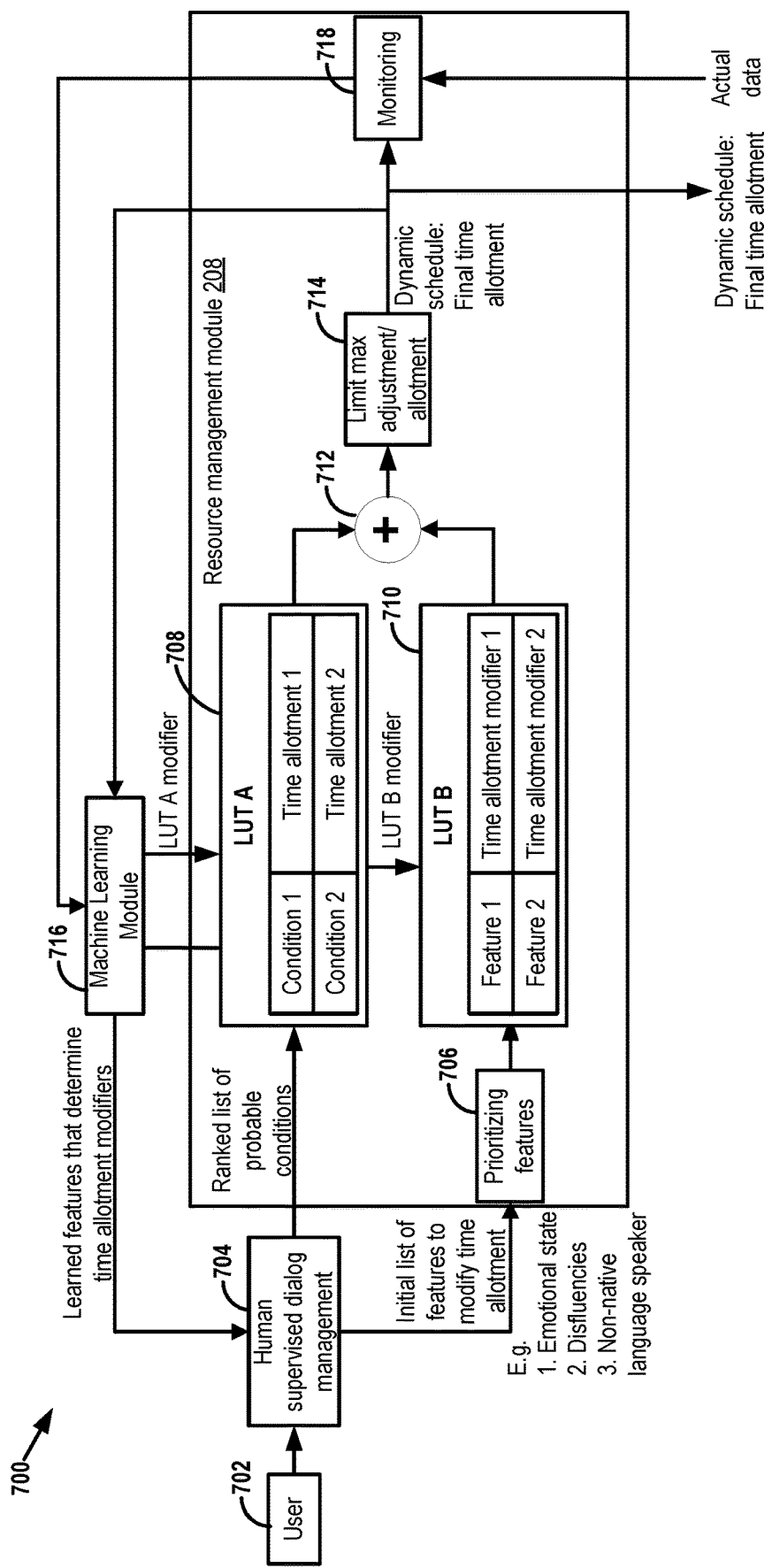
FIG. 7 is a conceptual diagram for scheduling a medical appointment for a user, according to techniques described herein.

FIG. 7 is a conceptual diagram 700 for scheduling a medical appointment for a user, according to techniques described herein. In some examples, one or more operations shown in FIG. 7 may be performed by computing system 102.

In some examples, the one or more operations shown in FIG. 7 may be performed after element 430 of flowchart 400 in FIG. 4. For example, subsequent to when the ranked list of most probable health condition or conditions are determined, computing system 102 creates a dynamic schedule for the user and for the health provider.

As described above, user 702 interacts with computing system 102 via a human supervised dialog management function 704. One of the outputs from this function is a ranked list of probable health conditions (e.g., as described above with reference to FIG. 6). In the example shown in FIG. 7, the ranked list of probable health conditions is input to the resource management module 208 of computing system that may include lookup table A (LUT A) 708. In some examples, LUT A 708 may contain a table of values that may be predetermined and preprogrammed, associating a probable health condition to a time allotment. As shown in FIG. 7, "Condition 1" is associated with "Time allotment 1" and "Condition 2" is associated with "Time allotment 2". For example, a probable health condition of "Dry cough" may have a time allotment of eight minutes while a probable health condition of "Wheezing" may have a time allotment of twelve minutes. In some examples, these associations may be determined through previous research or may be obtained through various means such as by interviewing experts or machine learning techniques applied to training data of previous appointments. While only two entries are shown in LUT A 708, LUT A 708 may contain fewer or more entries. In some examples, LUT A 708 may contain a default time allotment for a medical appointment.

Another output from the human supervised dialog management function (704) may be an initial list of features that describe the user or something about the user that may have impact on the time allotment (e.g., as described above with reference to FIG. 1). For example, if there a high emotional state is detected (potentially suggesting anxiety) or if disfluencies are detected (potentially suggesting confusion or an inability to understand medical terminology or conditions) or if a non-native English language speaker is detected, then each feature by itself or in combination may modify the time allotment. As shown in FIG. 7, resource management module 208 may include another look up table (LUT B) 710 that associates features to respective time allotment modifiers. In the example shown in FIG. 7, "Feature 1" is associated with "Time allotment modifier 1" and "Feature 2" is associated with "Time allotment 2". For example, a feature of a non-native English speaker may be associated with a time allotment modifier to increment the time allotment by five minutes and a feature of a high emotional state may be associated with a time allotment modifier of two minutes. While only two entries are shown in LUT B 710, LUT B 710 may contain fewer or more entries. The entries to LUT B 710 may be determined through previous research or may be obtained through various means such as by interviewing experts or machine learning techniques applied to training data of previous appointments. Once the modifier is determined, it is added to the time allotment associated with the probable condition. In some examples, resource management module 208 looks up one or more time allotments for one or more particular probable health conditions from LUT A 708 and looks up one or more time allotment modifiers corresponding to one or more features from LUT B 710 and aggregates the one or more time allotments and the one or more time allotment modifiers (712). In some examples, resource management module 208 aggregates the largest time allotment for the one or more probable health conditions with the time allotment modifiers associated with one or more features. In some examples, resource management module 208 aggregates the largest time allotment for the one or more probable health conditions with the largest time allotment modifier associated with one or more features. Computing system 102 then proposes one or more time slots for a medical appointment using the final aggregated time allotment. While described as lookup tables, LUT A 708 and LUT B 710 may in some cases represent databases, machine learning models, or other mapping of conditions to time allotment (LUT A 708) or feature to time allotment modifier (LUT B 710).

There may be many variations of this technique. As an example, resource management module 208 may include an algorithm to determine which of the list of features should be prioritized. In some examples, an order of priority may be preprogrammed in resource management module 208. For example, if the three features of emotional state, disfluencies, and non-native speaker are detected as shown in FIG. 7, resource management module 208 may prioritize the non-native English speaker feature over the other two features (e.g., use the time allotment modifier associated with a non-native English speaker feature). In some examples, the preprogramming may be to include or prioritize two or more features, and the two or more time allotment modifiers may be added to the particular time allotment determined from LUT A 708. In some examples, resource management module 208 may limit the maximum aggregated time allotted or the maximum time allotment adjustment for a medical appointment (714).

In some examples, resource management module 208 may monitor feedback data following the scheduled medical appointments (718). For example, the time allotment, the time allotment modifier(s), final aggregated time allotment, data related to how much time the medical appointment actually took (e.g., actual the duration for the medical appointment), the probable health condition(s), feature(s) of the user, and/or the clinical outcome of the medical appointment (e.g., the diagnosis of the health condition) are feed as input to monitor 718, which optionally logs the times (e.g., in knowledge database 216 or memory module 214 of FIG. 2). In some examples, these values are also fed into the machine learning module 716, which may update the time allotments and/or time allotment modifiers in LUT A 708 and/or LUT B, respectively, or update the guideline information (e.g., the normalized expressions). For example, machine learning module 716 may update a particular time allotments and/or a particular time allotment modifiers in LUT A 708 and/or LUT B based on the average actual time taken during the medical appoints for the respective potential health conditions and/or features (e.g., the actual duration for the medical appointment). In this way, as the utilization of computing system 102 increases, the amount of actual data feed back into the system also increases, which allows machine learning module 708 to better discern what features are better prioritized over others, as well as optimize values of the time allotments associated with a particular condition and the time allotment modifiers for each detected feature. In this way, computing system 102 may schedule medical appointments with more accurate time allotments to better utilize medical personnel, properly diagnose patients, and reduce wait times. In some examples, machine learning module 708 corresponds to machine learning engine 204 of FIG. 2.

Figure 8:
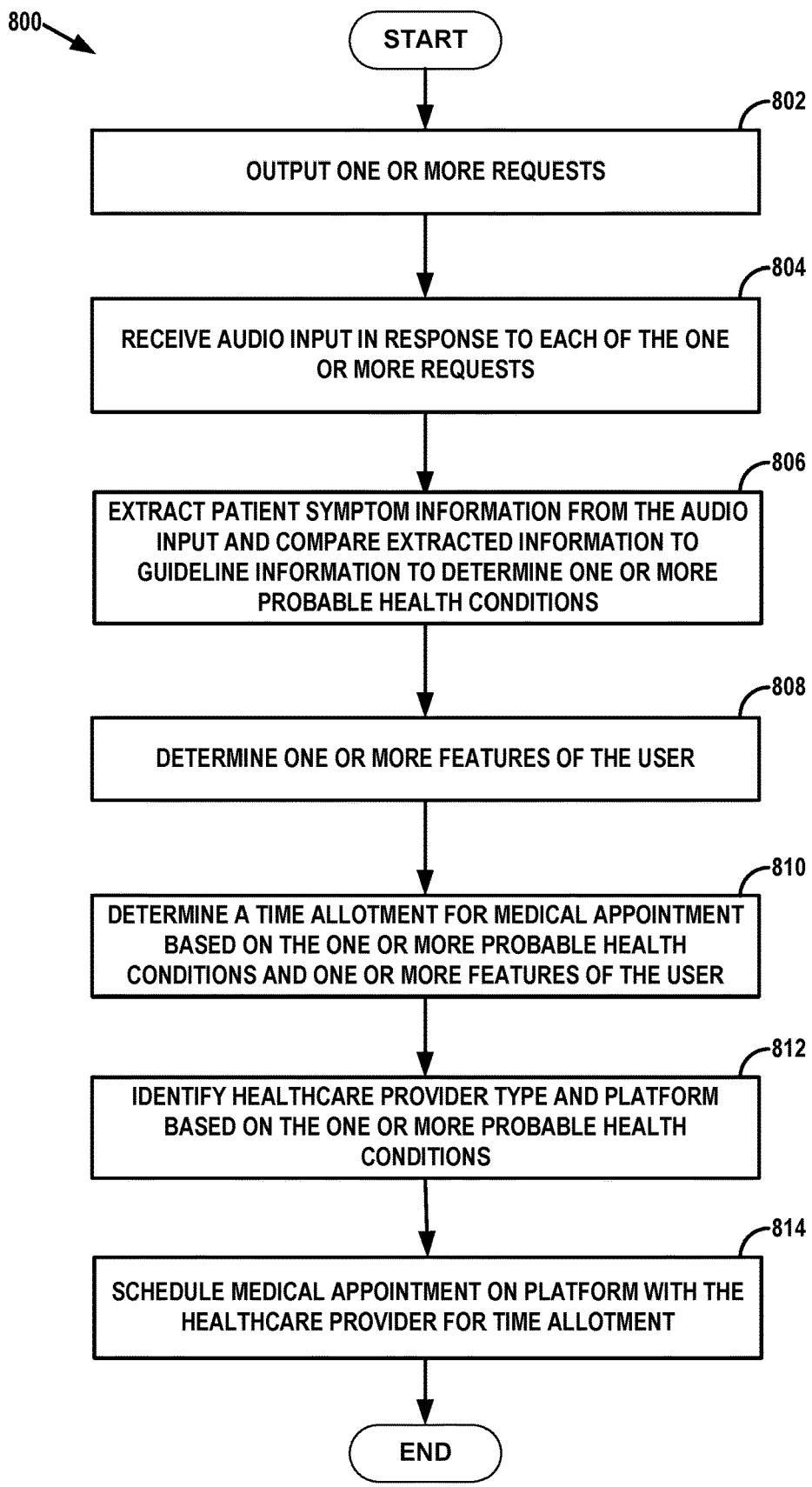
FIG. 8 is a flowchart illustrating example operations of a method for determining a time allotment, health care provider type, and/or platform for a medical appointment, according to techniques of this disclosure.

FIG. 8 is a flowchart 800 illustrating example operations of a method for determining a time allotment, health care provider type, and/or platform for a medical appointment, according to techniques of this disclosure. In some examples, one or more operations shown in FIG. 8 may be performed by computing system 102.

Computing system 102 may output one or more requests 150 for audio input 130 to user device 120 (802). For example, computing system 102 may stream one or more audio requests that are played on user device 120. In response to the one or more requests 150, computing system 102 may receive audio input 130 from user device 120 (804). For example, user 119 may then speak responses to each of the one or more requests 150 into user device 120, which communicates the responses as audio input 130 to computing system 102.

Computing system 102 may extract information from audio input 130 and compare the extracted information to clinical guideline information to determine one or more probable health conditions of user 119 (806). For example, computing system 102 may extract symptom information from complaints or statements in audio data 150 (e.g., from statement such as "I have a severe sore throat") or from other sounds in audio data 150 (e.g., from detecting coughing, wheezing, shortness of breath, sneezing, congestion, sniffling, confusion, disorientation, or any other non-verbal indications of probable symptoms of potential health conditions). In some examples, computing system 102 may compare the guideline information to at least one of electronic health data associated with the user (e.g., patient medical history), epidemiological data, or local area data to determine one or more probable health conditions of user 119, as described above. Either way, computing system 102 may formulate additional one or more requests 150 based on missing information corresponding to related clinical guidelines (e.g., clinical guidelines that match one or more symptoms or conditions that the user is experiencing or that relate to electronic health data associated with the user, epidemiological data, or local area data) to determine the one or more probable health conditions (e.g., the one or more clinical guidelines that most closely match the user's symptoms).

Computing system 102 also determines one or more features about user 119 based on the extracted information (808). For example, computing system 102 may determine whether the user is worried, nervous, confident, agitated, annoyed, or in any other emotional state. Computing system 102 may also detect disfluencies or whether the user 119 is a non-native language speaker. For example, computing system 102 may determine the "medical fluency" of user 119 (e.g., how well the user appears to understand medical terminology, health conditions, treatment options, etc.), which may require a longer time allotment. In some examples, computing system 102 may determine the one or more features concurrently or serially with extracting patient symptom information (e.g., steps 806 and 808 may be performed concurrently or serially). Either way, computing system 102 may determine a time allotment for a medical appointment based on the one or more probable health conditions and the one or more features of user 119 (810). As described above with reference to FIG. 7, computing system 102 may look up a time allotment associated with a probable health condition and look up one or more time allotment modifiers based on the one or more features, and modify the time allotment associated with a probable health condition of the user based on the one or more time allotment modifiers.

Computing system 102 may identify a health care provider type (e.g., a primary care physician, a specialist, or a nurse practitioner) from health care provider system 142, and a platform (e.g., in-person consultation, video consultation, telephone consultation, chat consultation, email consultation) for a medical appointment 132 based on the one or more probable health conditions and one or more features. In some examples, the computing system may identify a health care provider based on that providers schedule and/or skills or experience with the user's probable health condition. Computing system 102 may then schedule the medical 132 on the identified platform with the health care provider for the time allotment (814). For example, computing system 102 may provide a suggested time slot for the medical appointment with the health care provider for the time allotment to user device 120. User 119 may then approve the suggest time slot or request another time, another health care provider type, another health care provider, or another platform. In some examples, feedback information after the medical appointment may be entered into computing system 102 to improve the identification of relevant clinical guidelines, determination of potential medical conditions, and/or the time allotments for medical appointments. In this way, computing system 102 may schedule medical appointments with more accurate time allotments to better utilize medical personnel, properly diagnose patients, and reduce wait times.

The above examples, details, and scenarios are provided for illustration, and are not intended to limit the disclosure in any way. Those of ordinary skill in the art, with the included descriptions, should be able to implement appropriate functionality without undue experimentation. References in the specification to "an embodiment," "configuration," "version," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to affect such feature, structure, or characteristic in connection with other embodiments whether or not explicitly indicated.

Examples in accordance with the disclosure may be implemented in hardware, firmware, software, or any combination thereof. Modules, data structures, function blocks, and the like are referred to as such for ease of discussion and are not intended to imply that any specific implementation details are required. For example, any of the described modules and/or data structures may be combined or divided into sub-modules, sub-processes or other units of computer code or data as may be required by a particular design or implementation. In the drawings, specific arrangements or orderings of schematic elements may be shown for ease of description. However, the specific ordering or arrangement of such elements is not meant to imply that a particular order or sequence of processing, or separation of processes, is required in all embodiments.

In general, schematic elements used to represent instruction blocks or modules may be implemented using any suitable form of machine-readable instruction, and each such instruction may be implemented using any suitable programming language, library, application programming interface (API), and/or other software development tools or frameworks. Similarly, schematic elements used to represent data or information may be implemented using any suitable electronic arrangement or data structure. Further, some connections, relationships or associations between elements may be simplified or not shown in the drawings so as not to obscure the disclosure. This disclosure is to be considered as exemplary and not restrictive in character, and all changes and modifications that come within the spirit of the disclosure are desired to be protected.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules, engines, or components may be implemented together or separately as discrete but interoperable logic devices. Depiction of different features as modules, engines, or units is intended to highlight different functional aspects and does not necessarily imply that such modules, engines or units must be realized by separate hardware or software components. Rather, functionality associated with one or more modules, engines, or units may be performed by separate hardware or software components or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, processing circuitry, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), Flash memory, a hard disk, a CD-ROM, a floppy disk, a cassette, magnetic media, optical media, or other computer readable media. A computer-readable medium may include any mechanism for storing or transmitting information in a form readable by a machine. For example, a computer-readable medium may include any suitable form of volatile or non-volatile memory. In some examples, the computer-readable medium may comprise a computer-readable storage medium, such as non-transitory media. The term "non-transitory" may indicate that the storage medium is not embodied in a carrier wave or a propagated signal. In certain examples, a non-transitory storage medium may store data that can, over time, change (e.g., in RAM or cache).

What is claimed is:

1. A method for automatically scheduling medical appointments comprising:
    outputting, by a computing system, one or more requests for audio input to a user;
    receiving, by the computing system, the audio input in response to each of the one or more requests;
    extracting, by the computing system, patient symptom information from the audio input;
    applying, by the computing system, guideline information to the extracted patient symptom information to determine one or more probable health conditions for the user;
    determining, by the computing system, a time allotment for a medical appointment for the user based at least on the one or more probable health conditions for the user;
    wherein determining the time allotment for the medical appointment comprises:
        determining an estimated time allotment for the medical appointment based on the one or more probable health conditions;
        determining one or more features of user speech by the user from the audio input,
        obtaining respective time allotment modifiers for the one or more features of the user speech by the user, and
        modifying the estimated time allotment based on the respective time allotment modifiers for the one or more features of the user speech by the user to determine the time allotment for the medical appointment; and
    providing, by the computing system, a suggested time slot for the medical appointment with a health care provider for the time allotment for the medical appointment.

2. The method of claim 1, wherein determining the time allotment for the medical appointment comprises:
    obtaining respective expected time allotments for one or more probable health conditions for the user; and
    computing the time allotment for the medical appointment based at least on the respective expected time allotments for the one or more probable health conditions for the user.

3. The method of claim 1, further comprising:
    identifying a platform for the medical appointment based on the one or more probable health conditions; wherein scheduling the medical appointment includes scheduling the medical appointment with the health care provider for the identified platform.

4. The method of claim 3, wherein the platform comprises one of an in-person meeting with a medical professional, a telephone call with a medical professional, or a video call with a medical professional.

5. The method of claim 1, wherein obtaining respective time allotment modifiers for the one or more features of the user speech by the user comprises:
    obtaining, from a data structure that stores respective time allotment modifiers for features of user speech, the respective time allotment modifiers for the one or more features of the user speech by the user.

6. The method of claim 1, wherein the one or more features include one or more of an indication that the user is a non-native language speaker, an indication that the user is worried, an indication that the user is confident, an indication that the user is agitated, or an indication that the user has disfluencies.

7. The method of claim 1, further comprising:
    supervising, by a human operator of the computing system, the one or more requests and audio input;
    determining, by the computing system, an emotional characteristic of the user based on the audio input; and
    in response to a determination that the emotional characteristic is below a threshold, alerting the human operator.

8. A method for automatically scheduling medical appointments, comprising:
    outputting, by a computing system, one or more requests for audio input to a user;
    receiving, by the computing system, the audio input in response to each of the one or more requests;
    extracting, by the computing system, patient sympton information from the audio input;
    recieving, by the computing system, a plurality of clinical guidelines, the plurality of clinical guidelines comprising at least one of natural langugae text or a flow chart;
    extracting, by the computing system, a plurality of guideline key phrases from the plurality of clinical guidelines;
    normalizing, by the computing system, the plurality of guideline key phrases to one or more normalized guideline expressions;

applying, by the computing system, guideline information to the extracted patient sympton information to determine one or more probable health conditions for the user;

determining, by the computing system, a time allotment for a medical appointment for the user based at least on the one or more probable health conditions for the user; and providing, by the computing system, a suggested time slot for the medical appointment with a health care provider for the time allotment for the medical appointment.

9. The method of claim 8, wherein extracting the patient system information from the audio input includes:

applying, by the computing system, audio processing software to the audio input to produce text input;

extracting, by the computing system, a plurality of key input phrases from the text input; and comparing, by the computing system, the plurality of key input phrases to the one or more normalized guideline expressions, the method further comprising identifying, by the computing system, one or more relevant guidelines based on a number of the plurality of key input phrases matching the one or more normalized guidelines expressions being above a threshold, wherein the guideline information comprises the one or more relevant guidelines.

10. The method of claim 9, further comprising:

in response to the number of the plurality of key input phrases matching the one or more normalized guidelines being below the threshold, analyzing information from one or more of electronic health data, epidemiological data, or local area data to identify one or more relevant guidelines.

11. The method of claim 9, further comprising:

analyzing information from one or more of electronic health data, epidemiological data, or local area data to rank one or more relevant guidelines, wherein the guideline information comprises the ranked one or more relevant guidelines.

12. The method of claim 11, further comprising:

determining a most probable health condition of the user based on a top ranked relevant guideline of the ranked one or more relevant guidelines, and wherein determining the time allotment for the medical appointment comprises obtaining as expected time allotment corresponding to the most probable health condition.

13. The method of claim 11, wherein determining the one or more probable health conditions includes identifying the respective health conditions of associated with the ranked one or more relevant guidelines in ranking order.

14. A method for automatically scheduling medical appointments, comprising:

outputting, by a computing system, one or more requests for audio input to a user;

receiving, by the computing system, the audio input in response to each of the one or more requests;

extracting, by the computing system, patient symptom information from the audio input;

applying, by the computing system, guideline information to the extracted patient symptom information to determine one or more probable health conditions for the user;

determining, by the computing system, a time allotment for a medical appointment for the user based at least on the one or more probable health conditions for the user, providing, by the computing system, a suggested time slot for the medical appointment with a health care provider for the time allotment for the medical appointment;

determining one or more clinical inferences based on the extracted patient symptom information;

identifying one or more relevant clinical guidelines based on the one or more clinical inferences and at least one of electronic health data associated with the user, epidemiological data, or local area data, wherein the guideline information comprises the one or more relevant clinical guidelines; and determining, by the computing system, missing information based on application of the guideline information to the extracted patient sympton information, wherein at least one of the one or more requests are for the missing information.

15. The method of claim 14, further comprising:

storing the audio input within the electronic health data associated with the user.

16. The method of claim 1, further comprising:

applying the guideline information to at least one of electronic health data, epidemiological data, or local area data to determine the one or more probable health conditions for the user.

17. The method of claim 1, further comprising:

receiving feedback data after the medical appointment, the feedback data including an actual duration for the medical appointment; and adjusting a particular time allotment corresponding to at least one of the probable health conditions based at least on the feedback data.

18. A computing system for automatically scheduling medical appointments, the computing system comprising:

processing circuitry coupled to a memory;

a dialog manager executing on the processing circuitry and configured to output one or more requests for audio input to a user and receive the audio input in response to each of the one or more requests;

a speech analysis module executing on the processing circuitry and configured to extract patient symptom information from the audio input;

a machine learning engine executing on the processing circuitry and configured to apply guideline information to the extracted patient symptom information to determine one or more probable health conditions for the user; and a resource management module executing on the processing circuitry and configured to:

determine a time allotment for a medical appointment for the user based at least on the one or more probable health conditions for the user, wherein to determine the time allotment for the medical appointment the resouce management module is configured to:

determine an estimated time allotment for the medical appointment based on the one or more probable health conditions, determine one or more features of user speech by the user from the audio input, obtain respective time allotment modifiers for the one or more features of the user speech by the user, and modify the estimated time allotment based on the respective time allotment modifiers for the one or more features of the user speech by the user to determine the time allotment for the medical appointment;

and
provide a suggested time slot for the medical appointment with a health care provider for the time allotment for the medical appointment.

19. The computing system of claim 18, wherein the machine learning engine is further configured to:
receiving feedback data after the medical appointment, the feedback data including an actual duration for the medical appointment; and
adjusting a particular time allotment corresponding to at least one of the probable health conditions based at least on the feedback data.

20. A non-transitory computer-readable medium comprising instructions for causing processing circuitry of a computing system to perform operations comprising:
output one or more requests for audio input to a user;
receive the audio input in response to each of the one or more requests;
extract patient symptom information from the audio input;
apply guideline information to the extracted patient symptom information to determine one or more probable health conditions for the user;
determine a time allotment for a medical appointment for the user based at least on the one or more probable health conditions for the user, wherein to determine the time allotment for the medical appointment the processing circuitry is configured to:
determine an estimated time allotment for the medical appointment based on the one or more probable health conditions,
determine one or more features of user speech by the user from the audio input,
obtain respective time allotment modifiers for the one or more features of the user speech by the user, and
modify the estimated time allotment based on the respective time allotment modifiers for the one or more features of the user speech by the user to determine the time allotment for the medical appointment;
and
provide a suggested time slot for the medical appointment with a health care provider for the time allotment for the medical appointment.

* * * * *